Figure 1:
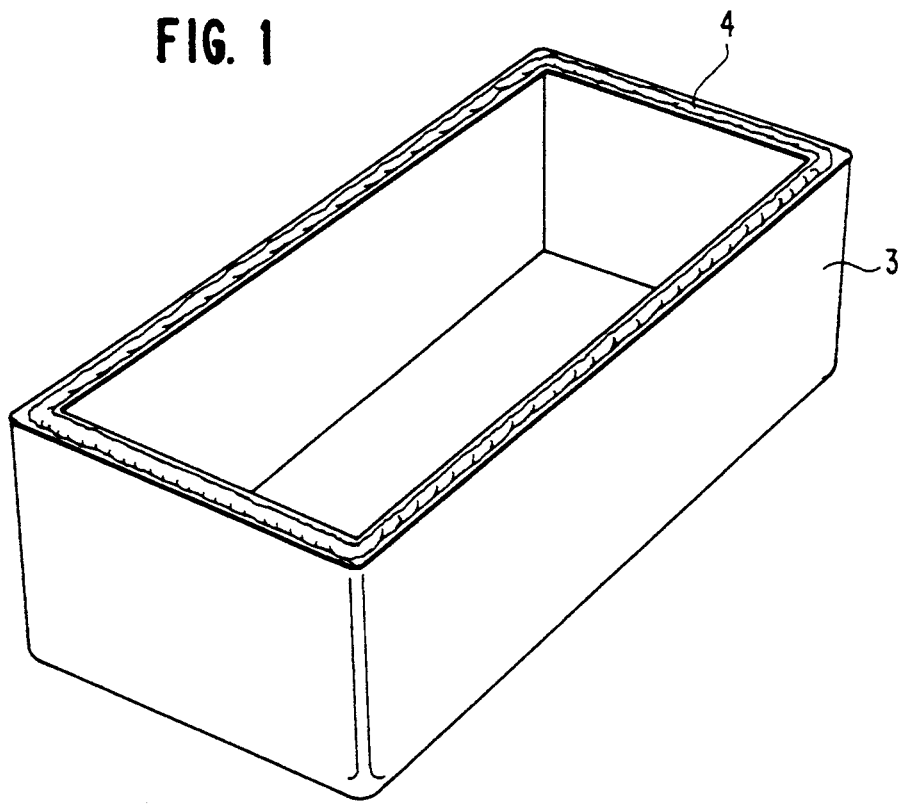

United States Patent [19]
Bongi

[11] Patent Number: 5,331,171
[45] Date of Patent: Jul. 19, 1994

[54] INSPECTION SYSTEM FOR CONTROLLING THE LAYING OF A STRING OR LAYER OF A FLUORESCENT MATERIAL ON A METAL PIECE

[75] Inventor: Adolfo Bongi, Turin, Italy

[73] Assignee: Comau S.p.A., Grugliasco, Italy

[21] Appl. No.: 102,423

[22] Filed: Aug. 5, 1993

[30] Foreign Application Priority Data

Sep. 30, 1992 [IT] Italy .......................... T092 A000794

[51] Int. Cl.$^5$ .............................................. G01N 21/64
[52] U.S. Cl. .............................. 250/461.1; 250/485.1; 250/458.1
[58] Field of Search ............... 250/461.1, 459.1, 458.1, 250/485.1

[56] References Cited

U.S. PATENT DOCUMENTS

| | | | |
|---|---|---|---|
| 3,617,744 | 11/1971 | Irish | 250/461.1 |
| 3,628,016 | 12/1971 | Berler | 250/461.1 |
| 4,598,205 | 7/1986 | Kaule et al. | 250/461.1 |
| 4,778,999 | 10/1988 | Fisher | 250/461.1 |
| 5,001,353 | 3/1991 | Odake et al. | 250/461.1 |

*Primary Examiner*—Paul M. Dzierzynski
*Assistant Examiner*—Drew A. Dunn
*Attorney, Agent, or Firm*—Sughrue, Mion, Zinn, Macpeak & Seas

[57] ABSTRACT

An optical inspection system for controlling the laying of a string or layer of a fluorescent material on a metal piece comprises an optical inspection station including a wall movable between an open condition and a closed condition in which the wall defines a dark chamber wherein the piece to be controlled is confined. With the wall there are associated Wood lamps which illuminate the piece ensuring an optimal inspection by the video camera.

2 Claims, 1 Drawing Sheet

U.S. Patent
July 19, 1994
5,331,171

INSPECTION SYSTEM FOR CONTROLLING THE LAYING OF A STRING OR LAYER OF A FLUORESCENT MATERIAL ON A METAL PIECE

The present invention relates to an optical inspection system for controlling the laying of a string or layer of a fluorescent material on a metal piece.

In motor-vehicle components, it is now a conventional technique to use so-called "structural" sealing materials and adhesives interposed between the elements of a structure, for example between the crankcase and the sump of an internal combustion engine in order to obtain both the required sealing effect and the required degree of strength of the structure.

Among the materials which are used, there are structural adhesives, for example an adhesive marketed under the trade-mark LOCTITE 573 ®, which have fluorescence properties.

In a mass production, where such materials are layed by means of automated systems, it is then necessary to provide a quality check of the laying of the string or layer of adhesive.

It has already been proposed to achieve the above-mentioned result by optical means comprising a vision system with a black-and-white video camera which inspects the piece while it is illuminated by a strong light, typically a neon light. However, the results achieved by such technology are not always satisfactory because the string, which usually has a surface with an irregular shape or in any case not uniform in cross-section, has a position relative to the light rays from the lamp which originates areas with an excess of light, particularly on the string, altering thereby the grey level sensed by the video camera. This originates great difficulties for the vision system which may sense such areas in different possible ways giving results which are not correct or have a low degree of reliability.

Furthermore, the pieces on which the sealing material is layed have irregular shapes with different depth. This originates a play of reflected light which affects the clearness of the contrast between the string and the piece.

In order to overcome such problems and considering that the materials in question have fluoresence properties, the present invention provides an optical inspection system of the above-indicated type, whose main characteristic is that such system comprises:

a transport line having piece supporting pallets for transporting the pieces to be controlled, an optical inspection station located on the path of said line, said station comprising:

wall means, movable between an opened condition and a closed condition in which they define a dark chamber wherein the piece to be controlled is confined, at least a Wood lamp provided on said wall means to light the piece to be controlled by ultra-violet light after that the piece has been confined in the dark chamber, video camera means supported by said wall means for optically inspecting the fluorescent material disposed on the piece to be controlled and lit by the ultra-violet light, and electronic means for processing output signals from said video camera and for providing data on the quality of the laying of the string of fluorescent material.

Due to said features, the system according to the invention is able to enhance the contrast string-piece and to eliminate almost completely the plays of reflected light caused by the shape of the piece itself, greatly increasing the reliability and reducing the errors at minimum.

Figure 2:
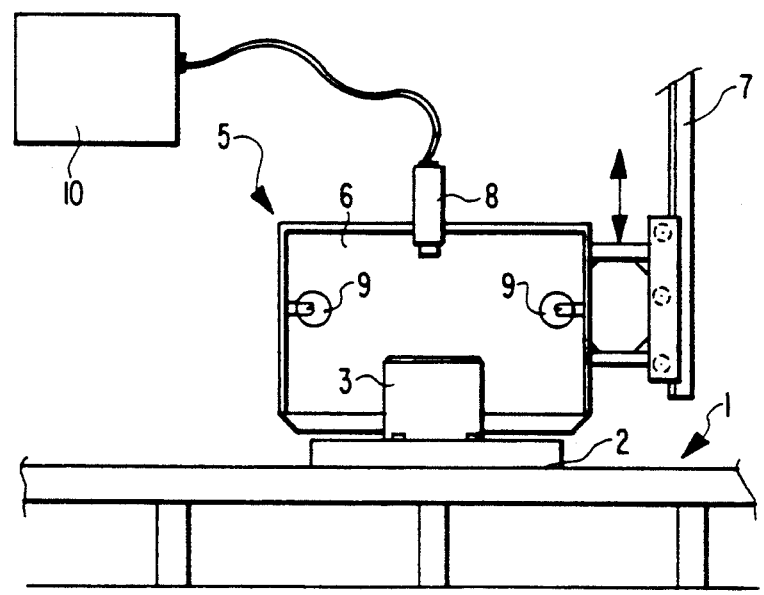

The invention will be now described with reference to the annexed drawings, given purely by way of non limiting example, in which:

FIG. 1 is a perspective diagrammatic view of a piece bearing a string of a fluorescent structural adhesive, and FIG. 2 is a diagrammatic elevational view of the system according to the invention.

With reference to the drawings, numeral 1 generally designates a transport line with pallets 2 each carrying a metal piece 3 (FIG. 1) on whose upper surface there has been previously layed, for example by a robot, a string of an adhesive, such as LOCTITE 573 ®. The string is indicated by reference numeral 4 in FIG. 1.

With specific reference to FIG. 2, numeral 5 generally designates a casing adapted to define a dark chamber 6 which is movable between a lowered position (illustrated in FIG. 2) and a raised position with respect to a support structure 7. The upper wall of casing 5 supports a video camera 8 which is to perform the optical inspection of string 4, whereas the side walls support a plurality of Wood lamps 9 adapted to light piece 3 by ultra-violet light once the latter has been confined within dark chamber 6.

In operation, line 1 is advanced intermittently, so as to stop each piece 3 in the position illustrated in FIG. 2 to allow optical inspection of the string 4. During movement of line 1, casing 5 is in its raised position. When a piece 3 is stopped in the inspection station, casing 5 is lowered in the position illustrated in FIG. 2 so as to confine piece 3 within dark chamber 6, whereupon the lamps 9 are turned on (they could also be kept constantly on) to light piece 3 by ultra-violet light, ensuring thereby an optimal optical inspection of the string by the video camera 8. The output signals by the video camera are processed by electronic means 10 (which form part of the vision system) to provide data on the quality of the laying of the string 4.

Tests conducted by the applicant have shown that the above-described system achieves efficient result both in case the fluorescent material forms a layer spread on the metal piece, for example with a thickness of about 0.1 mm and in case it forms a string with a thickness of about 1–2 mm and a width of 3–5 mm.

Under the light of the Wood lamps, the fluorescent string takes a colour tending to a very pale green, and is clearly visible by the video camera 8.

Naturally, the principle of the invention remaining the same, the construction details and the embodiments may widely vary with respect to what has been described and illustrated purely by way of example, without departing from the scope of the present invention.

I claim:

1. An optical inspection system for controlling the laying of a string or a layer of a fluorescent material on a metal piece, said system comprising:

a transport line with piece-supporting pallets for transporting pieces to be controlled, an optical inspection station located on the path of said line, said station comprising:

wall means movable between an opened condition and a closed condition in which said wall means define a dark chamber wherein the piece to be controlled is confined, at least a Wood lamp located on said wall means to illuminate said piece by ultra-violet light after that said piece has been confined within said dark chamber, video camera means supported by said wall means for optically inspecting the string of a fluorescent material on said piece, illuminated by the ultra-violet light of said at least a Wood lamp, and electronic means for processing output signals from said video camera means and to provide data on the quality of the laying of the string or layer of fluorescent material.

2. An optical inspection system according to claim 1, wherein said wall means include a casing opened downwardly, slidably mounted on a support structure between a raised position and a lowered position, said casing having an upper wall carrying said video camera means and side walls carrying said at least a Wood lamp.

* * * * *